United States Patent [19]

Parnell et al.

[11] Patent Number: 4,770,324

[45] Date of Patent: Sep. 13, 1988

[54] DENTAL CREAM PACKAGE

[75] Inventors: Marie B. Parnell, Stockport; Harry Hayes, Pendle, both of England

[73] Assignee: Colgate-Palmolive Company, New York, N.Y.

[21] Appl. No.: 922,872

[22] Filed: Oct. 31, 1986

Related U.S. Application Data

[63] Continuation-in-part of Ser. No. 808 756, Dec. 13, 1985, abandoned.

[51] Int. Cl.$^4$ .............................................. A61K 7/16
[52] U.S. Cl. ..................................... 222/107; 425/55; 425/49; 425/58; 425/57; 222/391
[58] Field of Search ............................. 424/49, 55, 57; 222/105, 107, 405, 391

[56] References Cited

U.S. PATENT DOCUMENTS 3,260,410  7/1966  Brandt .................................. 222/107
4,418,841  12/1983  Eckstein .............................. 222/107
4,437,591  3/1984  von Schuckmann ............... 222/405

FOREIGN PATENT DOCUMENTS 75410  4/1985  Japan .
1471215  4/1977  United Kingdom .

Primary Examiner—Ronald W. Griffin
Assistant Examiner—F. T. Moezie
Attorney, Agent, or Firm—Robert L. Stone; Murray M. Grill

[57] ABSTRACT

Dental cream in contact with a polyolefin resin surface of a package such as a laminate tube, a mechanical dispenser or a flexible sachet. The dental cream contains a dentally acceptable water-insoluble alkaline earth metal salt, a liquid vehicle and an alkali metal carboxymethyl cellulose gelling agent. The liquid vehicle contains water, glycerine and sorbitol and, as an additive to prevent syneresis due to contact between the dental cream and polyolefin resin, a stabilizer in the form of parahydroxybenzoate ester.

16 Claims, No Drawings

DENTAL CREAM PACKAGE

This application is a continuation-in-part of copending application Ser. No. 808,756, filed Dec. 13, 1985, now abandoned.

This invention relates to a dental cream packaged in a plastic laminate tube, mechanical dispenser, flexible sachet or the like. In particular it relates to a dental cream in compatible contact with a polyolefin surface of a package such as a plastic laminate dental cream tube, mechanical dispenser or flexible sachet.

Dental creams have been packaged for many years in flexible metal tubes such as wax lined lead tubes, unlined aluminium tubes or aluminium tubes having an epoxy resin lacquer coating thereon. In recent years flexible form-retaining laminated plastic tubes have been increasingly used.

Plastic laminated dental cream tubes typically comprise an inner polyolefin resin layer which is in direct contact with the dental cream and at least one intermediate layer, including an aluminium foil layer which inhibits loss of flavor from the dental cream. Desirably, an intermediate paper layer which provides stiffness to the tube is also present. The outer layers are typically of polyolefin resins, one of which may be colored white and bears printed indicia with a clear polyolefin laminate overlay to protect the indicia. Additional intermediate laminate layers or flexible plastic may also be present.

Mechanical dental cream dispensers may also have a polyolefin surface in contact with dental cream contained therein. In fact, the polyolefin itself may be the housing of the dispenser. Flexible sachet packets may also have a polyolefin surface in contact with dental cream.

Dental creams typically contain a liquid vehicle of water and humectant, a gelling agent solid vehicle and a water insoluble dental polishing agent. Dental creams composed of such materials wherein the humectant comprises glycerine and sorbitol and the polishing material is an alkaline earth metal salt such as dicalcium phosphate have been successfully packaged in flexible metal toothpaste containers including aluminium tubes having an internal coating of epoxy resin lacquer layer. However, it is observed that when such dental creams are packaged in containers having an interior polyolefin surface such as plastic laminated dental cream tubes, mechanically operated dental cream dispensers and flexible sachets, that syneresis occurs and liquids separate from the body of the dental cream, rendering the dental cream undesirable.

It is an advantage of this invention that phase separation of a dental cream packaged in contact with a polyolefin material is substantially prevented. Other advantages will be apparent from consideration of the following disclosure.

In accordance with certain of its aspects, this invention relates to a packaged dental cream wherein said dental cream is in direct contact with a polyolefin resin surface, said dental cream comprising at least about 20% by weight of a liquid vehicle comprising water, glycerine and sorbitol with a preservative as a stabilizer against syneresis, the weight ratio of glycerine to sorbitol being from about 0.25:1 to about 3:1, a dental cream solid vehicle comprising about 0.1-5% by weight of alkali metal carboxymethyl cellulose dental cream gelling agent, about 20-75% by weight of a dentally acceptable water-insoluble alkaline earth metal salt polishing agent and at least about 0.1% by weight of a $C_{1-4}$ alkyl parahydroxybenzoate ester as said preservative.

In dental cream formulations, the liquids and solids are necessarily proportioned to form a creamy mass of desired consistency which is extrudible from its package. The liquids in the present dental cream comprise chiefly water, glycerine and sorbitol. The total liquid vehicle comprises at least about 20% by weight of the dental cream and will generally be about 20-75% by weight. Alkali metal carboxymethyl cellulose is employed as a dental cream gelling agent or gum. Sodium carboxymethyl cellulose is preferred. The gelling agent content is about 0.1-5% and preferably about 0.5-2% by weight of formulation.

Water is generally incorporated into the dental cream in amount of about 10-50% by weight, preferably about 15-35%. Glycerine and sorbitol together generally comprise about 15-50% by weight, preferably about 20-35% of the dental cream, with the weight ratio of glycerine to sorbitol being from 0.25:1 to about 3:1, typically from about 0.25:1 to about 0.8:1 and preferably from about 0.6:1 to about 0.8:1. Amounts of sorbitol as used herein are of sorbitol syrup, as commercially available, that is 70% by weight sorbitol in 30% by weight of water.

A member of the "paraben" family of preservatives may be added to a preferred minimum level of 0.25% to prevent the dental cream from undergoing syneresis when in direct contact with a polyolefin resin surface of a dental cream package.

Adequate preservation of the product is also insured against bacterial contamination at such levels irrespective of the susceptibility of the basic formula. The paraben materials employed are $C_{1-4}$ alkyl parahydroxybenzoate esters, typically containing a 1 to 4 carbon alkyl group, that is methyl-, ethyl-, propyl- or butyl-parahydroxybenzoate as well as mixtures thereof, e.g. a weight ratio of about 1:5 to 5:1. Methyl parahydroxybenzoate (Nipagin M) and 1:1 weight mixture of methyl- and butyl parahydroxybenzoate (Nipastat) are preferred. Typically, the paraben is present in amount of about 0.1-5% by weight preferably about 0.25-1%.

Dentally acceptable water-insoluble alkaline earth metal salt polishing agent is present in the dental cream in amount of about 20-75% by weight, preferably about 35-60%. Typical salts include dicalcium phosphate dihydrate, anhydrous dicalcium phosphate, calcium carbonate, tricalcium phosphate, calcium pyrophosphate, dimagnesium phosphate trihydrate and magnesium carbonate including mixtures thereof; most preferred is calcium salt, particularly dicalcium phosphate dihydrate or mixture of dicalcium phosphate dihydrate and anhydrous dicalcium phosphate.

In addition to the alkaline earth metal salt polishing agent, additional polishing agent such as hydrated alumina and calcined alumina may be present, for instance in a weight ratio of alkaline earth metal salt to alumina material of about 2.5:1 to about 4:1, the total amount of polishing material in the dental cream being about 25-75% by weight.

Organic surface-active agents may be used in the dental cream of the present invention to achieve increased prophylactic action, assist in achieving thorough and complete dispersion of the instant compositions throughout the oral cavity, and render the dental creams more cosmetically acceptable. The organic surface-active material may be anionic, nonionic, ampholytic or cationic in nature, and it is preferred to employ as the surface-active agent a detersive material which imparts to the composition detersive and foaming properties. Suitable types of such detergents are water-soluble salt of higher fatty acid monoglyceride monosulphates, such as the sodium salt of the monosulphated monoglyceride of hydrogenated coconut oil fatty acids, higher alkyl sulphate, such as sodium lauryl sulphate, alkylaryl sulphonates, such as sodium dodecyl benzene sulphonate, olefinsulphonates, such as sodium olefin sulphonate in which the olefin group contains 12-22 carbon stoms, higher alkyl sulphoacetates, higher fatty acid ester of 1,2-dihydroxy propane sulphonates, and the substantially saturated higher aliphatic acyl amides of lower aliphatic amino carboxylic acid aompounds such as those having 12 to 16 carbon atoms in the fatty acid, alkyl or acyl radicals and the like. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of these compounds in compositions or the present invention. The amides are particularly advantageous since they exhibit a prolonged and marked effect in the inhibition of acid formulation in the oral cavity due to carbohydrated breakdown in addition to exerting some reduction in the solubility of teeth enamel in acid solutions. Another desirable material is a long chain fatty acid sodium monoglyceride sulphonate used alone or in combination with sodium lauryl sulphate.

Other particularly suitable surface-active materials include nonionic agents such as condensates of sorbitan monostearate with approximately 20 moles of ethylene oxide, condensates of ethylene oxide with propylene glycol ("Pluronic" materials) and amphoteric agents such as long chain (alkyl)amino-alkylene alkylated amine derivatives, which are available under the trademark "Miranol" such as Miranol C$_2$M. Cationic surface-active germicides and antibacterial compounds such as di-isobutyl phenoxy ethoxy ethyl dimethyl benzyl ammonium chloride, benzyl dimethyl stearyl ammonium chloride, benzyl diethyl stearyl ammonium chloride, tertiary amines having one fatty alkyl group (of from 12-18 carbon atoms) and two (poly)oxyethylene groups attached to the nitrogen (typically containing a total of from about 2 to 50 ethanoxy groups per molecule) and salts thereof with acids, and compounds of the structure

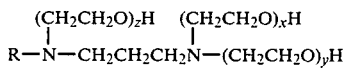

where R is a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the dental cream. It is most preferred that the surface-active agent be an anionic material, particularly sodium lauryl sulphate.

The dental cream suitably may also contain a fluorine-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride, (SnF$_2$.KF), sodium hexafluorostannate, stannous chlorofluoride, sodium fluorozirconate, and sodium monofluorophosphate. These materials which disassociate or release fluorine-containing ions in water, suitably may be present in an effective but non-toxic amount, usually within the range of about 0.01 to 1% by weight of the water soluble fluorine content thereof.

The preferred fluorine-containing system is sodium monofluorophosphate typically present in an amount of about 0.076 to 7.6% by weight, preferably 0.76% or a mixture of sodium monofluorophosphate and sodium fluoride desirable, for instance in a weight ratio of about 2:1 based on fluoride. When the sodium fluoride is present in addition to the sodium monofluorophosphate, a mixture of 1:1 fluoride from each is also desirable. The total preferred amount of soluble fluoride is about 1000-1500 ppm.

Any suitable flavoring or sweetening materials may be employed in formulating a flavor for the composition of the present invention. Examples of suitable flavoring constituents include the flavoring oils, e.g., oils of spearmint, peppermint, wintergreen, sassafras, clove, sage, eucalyptus, marjoram, cinnamon, lemon and orange as well as methyl salicylate. Suitable sweetening agents include sucrose, lactose, maltose, xylitol, sodium 6-methyl-3,4-dihydro-1,2,3-oxathiazine-4-one, sodium cyclamate, perillartine and sodium saccharin. Suitably, flavor and sweetening agents may together comprise from about 0.01 to 5% or more of the compositions of the instant invention.

There may be employed also various calcium and magnesium ion suppression agents for adjustment of physical properties of the compositions. Suitable agents are the water-soluble inorganic polyphosphate salts, such as tetrasodium pyrophosphate or disodium diacid pyrophosphate, with the partially neutralized or acid polyphosphate preferred. Other suitable agents are the alkali metal, preferably sodium, salts of citric acid. In general, such compounds will be a minor amount or proportion of the formulation, such as the physical characteristics of the dental cream, but will usually be from about 0.1% to about 3% by weight.

The dental creams should have a pH practicable for use. A pH range of 5 to 10 is particularly desirable. The reference to the pH is meant to be the pH determination directly on the dental cream. If desired, materials such a citric acid may be added to adjust to the pH to, say, 6 to 7.

Various other materials may be incorporated in the dental cream. Examples thereof are coloring or whitening agents or dyestuffs, anti-corrosive agents, silicones, chlorophylic compounds, ammoniated materials such as urea, diammonium phosphate and mixtures thereof and other constituents. Whitening agents, such as titanium dioxide, typically in amounts of about 0.5-2%, may be beneficial to the appearance of the dental composition, since upon aging, some discoloration may occur.

The adjuvants are incorporated in the instant composition in amounts which do not substantially adversely affect the properties and characteristics desired and are selected and used in proper amounts depending upon the particular type of composit involved.

Antibacterial agents may also be employed in the oral compositions of the instant invention in an amount of about 0.01-5% by weight. Typical antibacterial agents include:

$N^1$-(4-chlorobenzyl)-$N^5$-(2,4-dichlorobenzyl)biguanide;
p-chlorophenyl biguanide;
4-chlorobenzyhydryl biguanide;
4-chlorobenzhydrylguanylurea;
N-3-lauroxypropyl-$N^5$-chlorobenzylbiguanide;
1,6-di-chlorophenylbiguanidohexane;
1,6-bis-(2-ethylhexylbiguanide)hexane;
1-(lauryldimethylammonium)-8-(p-chlorobenzyldimethylammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine and their non-toxic acid addition salts.

The package into which the dental cream is incorporated may be any polyolefin laminate dental cream tube. For instance, the tube may be as elementary as is described in U.S. Pat. No. 3,260,410 to Brandt et al, the disclosure of which is incorporated herein by reference. As described in the example thereof, an aluminium foil base having a thickness of about 0.0013 cm was heated to a temperature of approximately 177° C., and one face of the heated foil was contacted by an extrudable film of a random copolymer of ethylene and acrylic acid (acid content 3±0.5% and melt index 8±1), while the opposite surface thereof had placed thereagainst a film of low density polyethylene.

Using driven rolls, a laminated base was obtained in which the copolymer layer was about 6 mils and the polyethylene layer was approximately 5 mils in thickness. The base was then shaped into tubular form and sealed.

After severing the tubular form into tube bodies, the tubes can be packed with the dental cream of the present invention without the dental cream undergoing syneresis.

Polyolefin laminate dentifrice tubes containing more intermediate layers may also be successfully used with the dental cream of the present invention without undergoing syneresis. For instance, the multiple layer flexible sheet structure for dental cream tubes described as "Prior Art" in U.S. Pat. No. 4,418,841 to Eckstein is incorporated herein by reference. In fact, dental cream of the present invention packed in tubes of sheet material identified as Prior Art A and A-1 in U.S. Pat. No. 4,418,841 are satisfactory and undergo substantially no syneresis. Such tubes A and A-1 are comprised of layers as set forth below, in the order of outermost layer to innermost layer.

| A | A-1 |
| --- | --- |
| 1.5 mil LDPE | 1.5 mil LDPE |
| 2.0 mil Pigmented LDPE | 2.0 mil Pigmented LDPE |
| 1.6 mil Paper | 1.6 mil Paper |
| 0.7 mil LDPE | 2.0 mil LDPE |
| 3.3 mil EAA | 1.0 mil OPP |
| 0.7 mil Foil | 1.0 mil EAA |
| 2.0 mil EAA | 0.7 mil Foil |
| 1.2 mil LDPE | 2.0 mil EAA |
| 13.0 mil Total | 1.2 mil LDPE |
| | 13.0 mil Total |

In A and A-1 the abbreviations have the following meanings:
LDPE: low density polyethylene
EAA: ethylene acrylic acid
OPP: oriented polypropylene Mechanically operated dispensers, such as the dispenser for, in particular, pasty substances, described in U.S. Pat. No. 4,437,591 to von Schuckmann, the disclosure of which is incorporated herein by reference, may also be used with the practice of the present invention. The housing of such dispensers is commonly composed of polyolefin resin such as polypropylene. Thus the housing resin is in essence a layer, the inner surface of which is in contact with dental cream. When the dental cream of the present invention is packaged in such a polypropylene mechanical dispenser, it undergoes substantially no syneresis.

The advantages of the invention are also present when the dental cream is packed in a flexible sachet having a polyolefin surface, typically of low density or medium density polyethylene.

The following illustrative examples are further indicative of the nature of the present invention but it is understood that the invention is not limited thereto. All amounts and proportions are by weight except as otherwise indicated.

EXAMPLE 1

The following dental creams are prepared to creamy consistencies and packed into tubes of each of laminated structures A and A-1, set forth above:

| | Parts | |
| --- | --- | --- |
| | (1) | (2) |
| Glycerine | 6.000 | 6.000 |
| Sodium Monofluorophosphate | 0.760 | 0.760 |
| Sodium Fluoride | 0.100 | 0.100 |
| Sodium Carboxymethyl cellulose | 0.900 | 0.900 |
| Tetrasodium Pyrophosphate | 0.250 | 0.250 |
| Sodium Saccharin | 0.200 | 0.200 |
| Sorbitol - 70% solution | 24.000 | 24.000 |
| Methyl Parahydroxybenzoate (Nipagin M) | 0.250 | — |
| Deionized water-irradiated | 16.923 | 17.173 |
| Dicalcium phosphate dihydrate | 48.000 | 48.000 |
| Flavor | 0.950 | 0.950 |
| Sodium lauryl sulfate (90% A.I.) | 1.667 | 1.667 |

After aging for at least 9 weeks at 49° C. dental cream (1) remains creamy in consistency in each of laminate tubes of structures A and A-1, whilst dental cream (2) separates into liquid and solid phases within 3 to 6 weeks at 49° C. in both of tubes of structures A and A-1.

EXAMPLE 2

Dental Creams (1) and (2) are incorporated into a mechanical dispenser in accordance with U.S. Pat. No. 4,437,591 composed of polypropylene housing. Dental cream (1) retains its creamy consistency whilst dental cream (2) separates into liquid and solid phases.

Similar results to those described above are observed when:
(i) calcium carbonate replaces dicalcium phosphate dihydrate;
(ii) dimagnesium phosphate trihydrate replaces dicalcium phosphate dihydrate;
(iii) the comparative amounts of glycerine and sorbitol (70%) are 10:15:0.25 vs. 10:15:0 and 6:24:1 vs 6:24:0;
(iv) methyl parahydroxybenzoate is replaced by ethyl parahydroxybenzoate; propyl parahydroxybenzoate; butyl parahydroxybenzoate; and 5:1, 1:1 and 1:5 mixtures of methyl parahydroxybenzoate and butyl parahydroxybenzoate, respectively;
(v) the dental creams are packed in laminated tubes in accordance with U.S. Pat. No. 3,260,410;

(vi) the dental creams are packed in crack resistant laminated tubes in accordance with U.S. Pat. No. 4,418,841;

(vii) the dental creams are packed in flexible sachets of the following structure from outermost to innermost layer:

12.2μ polyethylene terephthalate
21.3μ white ethylene acrylic acid
9.0μ foil
3.3μ ethylene acrylic acid
25.4μ medium density polyethylene.

When dental cream (1) is modified to employ 0.1 part of methyl parahydroxybenzoate the aging results continue to be better than is observed with dental cream (2) for up to 6 weeks at 49° C. Thereafter, separation does occur with dental cream under accelerated aging conditions.

It is understood that the foregoing detailed description is given merely by way of illustration and that variations may be made therein without departing from the spirit of the invention.

We claim:

1. A packaged dental cream wherein said dental cream is in direct contact with a low or medium density polyethylene or polypropylene surface, wherein syneresis occurs in said dental cream due to said direct contact, wherein said dental cream consists essentially of as ingredients of an aqueous vehicle at least about 20% by weight of said dental cream of liquid vehicle of water, glycerine and sorbitol, the amount of glycerine and sorbitol together being about 15-50% by weight of said dental cream; the weight ratio of glycerine to sorbitol being from about 0.25:1 to about 3:1; a dental cream solid vehicle of about 0.1-5% by weight of said dental cream of alkali metal carboxymethyl cellulose dental cream gelling agent; and about 20-75% by weight of said dental cream of a dentally acceptable water-insoluble calcium or magnesium alkaline earth metal salt polishing agent; said dental cream consisting essentially of said ingredients and as a preservative additive which prevents syneresis in said dental cream upon said direct contact at least 0.1% by weight of said dental cream of $C_{1-4}$ alkyl parahydroxybenzoate ester as said preservative.

2. The packaged dental cream claimed in claim 1 wherein the weight ratio of glycerine to sorbitol is from about 0.25:1 to about 0.8:1.

3. The packaged dental cream claimed in claim 2 wherein the weight ratio of glycerine to sorbitol is from about 0.6:1 to about 0.8:1.

4. The packaged dental cream claimed in claim 1 wherein said preservative is present in amount of about 0.25-1% by weight.

5. The packaged dental cream claimed in claim 4 wherein said preservative is methyl parahydroxybenzoate.

6. The packaged dental cream claimed in claim 5 wherein said preservative is a mixture of two of said alkylparahydroxybenzoate esters in a weight ratio of about 1:5 and 5:1.

7. The packaged dental cream claimed in claim 6 wherein said alkyl parahydroxybenzoate esters are methyl and butyl parahydroxybenzoates.

8. The packaged dental cream claimed in claim 6 wherein said alkyl parahydroxybenzoate esters are present in amount of about 1:1.

9. The packaged dental cream claimed in claim 1 wherein said alkali metal carboxymethyl cellulose is sodium carboxymethyl cellulose.

10. The packaged dental cream claimed in claim 9 wherein said sodium carboxymethyl cellulose is present in amount of about 0.5-2%.

11. The packaged dental cream in claim 1 wherein said water-insoluble alkaline earth metal salt is a calcium salt selected from the group consisting of at least one of dicalcium phosphate dihydrate, anhydrous dicalcium phosphate, calcium carbonate, tricalcium phosphate and calcium pyrophosphate.

12. The dental cream claimed in claim 11 wherein said calcium salt is dicalcium phosphate dihydrate.

13. The packaged dental cream claimed in claim 1 wherein said dental cream is packaged in a plastic laminate tube the inner surface of which is polyethylene.

14. The packaged dental cream claimed in claim 1 wherein said polyethylene is low density polyethylene.

15. The packaged dental cream claimed in claim 1 wherein said dental cream is packaged in a mechanical dispenser having a housing of polypropylene resin.

16. The packaged dental cream claimed in claim 1 wherein said dental cream is packaged in a flexible sachet, the inner surface of which is low density polyethylene or medium density polyethylene.

* * * * *